United States Patent [19]

Albarella et al.

[11] 4,399,121

[45] Aug. 16, 1983

[54] IODOTHYRONINE IMMUNOGENS AND ANTIBODIES

[75] Inventors: James P. Albarella; Robert J. Carrico; Thomas M. Li, all of Elkhart, Ind.

[73] Assignee: Miles Laboratories, Inc., Elkhart, Ind.

[21] Appl. No.: 363,084

[22] Filed: Mar. 29, 1982

Related U.S. Application Data

[63] Continuation-in-part of Ser. No. 318,026, Nov. 4, 1981, Pat. No. 4,358,604.

[51] Int. Cl.³ .................... A61K 39/00; A61K 37/00; C07C 103/52; C07C 101/32; C07C 67/00

[52] U.S. Cl. .............................. 260/112.5 R; 424/177; 560/40; 562/447; 560/210

[58] Field of Search ........................ 560/40, 210, 447; 424/177, 12; 260/112.5 R

[56] References Cited

U.S. PATENT DOCUMENTS 4,358,604 11/1982 Albarella et al. ..................... 560/40

Primary Examiner—Delbert R. Phillips
Attorney, Agent, or Firm—Andrew L. Klawitter

[57] ABSTRACT

Immunogen conjugates comprising N-aminoalkyl derivatives of iodothyronines, e.g., thyroxine and its lower alkyl esters, coupled to an immunogenic carrier material, and antibodies raised against such immunogen conjugates.

23 Claims, 2 Drawing Figures

PREPARATION OF
N-AMINOALKYL IODOTHYRONINE DERIVATIVES

IODOTHYRONINE IMMUNOGENS AND ANTIBODIES

CROSS-REFERENCE TO RELATED APPLICATION

This is a continuation-in-part of application Ser. No. 318,026, filed Nov. 4, 1981, now U.S. Pat. No. 4,358,604 issued Nov. 9, 1982.

BACKGROUND OF THE INVENTION

1. Field of the Invention

This invention relates to immunogen conjugates comprising iodothyronine derivatives, particularly aminofunctionalized derivatives, coupled to conventional immunogenic carrier materials, and antiiodothyronine antibodies prepared against such immunogen conjugates. Such antibodies are useful in immunoassays for determining iodothyronines in biological fluids.

The iodothyronines have the following general formula:

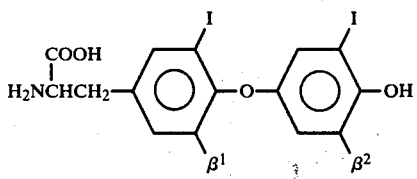

wherein $\beta^1$ and $\beta^2$ are, independently, hydrogen or iodine. The iodothyronines of clinical interest are listed in the following table:

| Iodothyronine | $\beta^1$ | $\beta^2$ |
| --- | --- | --- |
| 3,5,3'5'-tetraiodothyronine (thyroxine; T-4) | iodine | iodine |
| 3,5,3'-triiodothyronine (liothyronine; T-3) | iodine | hydrogen |
| 3,5',5'-triiodothyronine ("reverse" T-3) | hydrogen | iodine |
| 3,3'-diiodothyronine | hydrogen | hydrogen |

The quantitative determination of the concentration of the various iodothyronines, particularly the hormones T-3 and T-4, in serum and of the degree of saturation of the iodothyronine binding sites on the carrier protein thyroid binding globulin (TBG) are valuable aids in the diagnosis of thyroid disorders.

2. Brief Description of the Prior Art

Iodothyronines have been derivatized in many different ways in coupling them to immunogenic carrier materials for the purpose of preparing immunogen conjugates. Antibodies prepared against such conjugates are used in immunoassays for determining iodothyronines. Also, iodothyronines have been variously derivatized in order to couple a desired labeling moiety yielding a labeled conjugate useful in such immunoassays.

The commonly used technique for preparing iodothyronine immunogen conjugates involves coupling the iodothyronine directly through its available amino and carboxyl groups to amide bond carboxyl and amino counterpart groups on the carrier material in the presence of carbodiimide. A mixture of conjugates is obtained and consequently a mixture of anti-iodothyronine antibodies are obtained. See Gharib et al, *J. Clin. Endocrinol* 33:509(1971).

U.S. Pat. No. 4,171,432 describes the coupling of a ribonucleotide to iodothyronines through the carboxyl group. U.S. Pat. No. 4,040,907 describes the coupling of enzymes with iodothyronine derivatives derivatized at the phenolic hydroxyl group.

The preparation of aminoacyl thyroxine derivatives derivatized at the amino group of thyroxine is described in *Endocrinol.* 89:606–609(1971).

SUMMARY OF THE INVENTION

The present invention provides iodothyronine immunogen conjugates of immunogenic carriers coupled to iodothyronine derivatives bearing an aminofunctionalized arm at the amino group in iodothyronines and their alkyl esters. The immunogens provided are of the general formula:

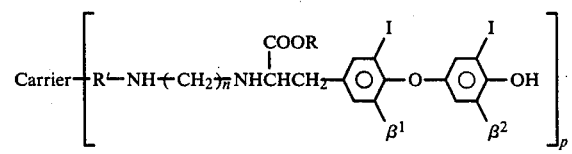

wherein Carrier is an immunogenic carrier material, R' is a bond or a linking group, n is an integer from 2 through 12, p is on the average from 1 through about 50, R is hydrogen or alkyl containing 1–6 carbon atoms, and $\beta^1$ and $\beta^2$ are, independently, hydrogen or iodine. When bridge group R' is a bond, the iodothyronine derivative is coupled directly to the carrier material, for example by amide linkages between the amino group in the iodothyronine derivative and carboxyl groups in the carrier, which in such case is usually a protein or polypeptide. When bridge group R' is other than a simple bond, it may comprise a wide variety of structures, for example, the residue of bifunctional linking agents coupling the amino group in the iodothyronine derivative to amino groups in the carrier, again usually a protein or polypeptide.

DESCRIPTION OF THE PREFERRED EMBODIMENTS

Figure 1:
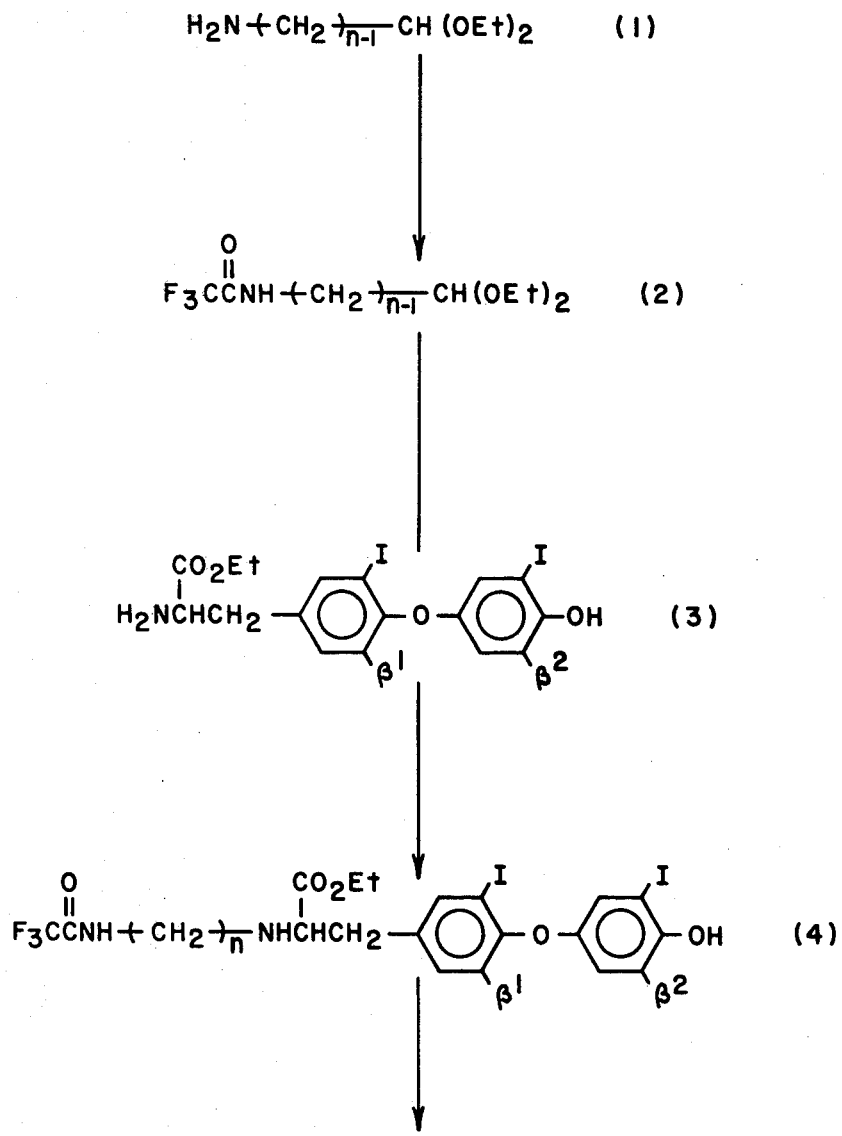
FIGS. 1 and 1a constitute a flow diagram of the synthetic route illustrated in the Examples for preparing the iodothyronine derivatives that are coupled to immunogenic carriers to form the immunogen conjugates of the present invention.
Figure 1A:
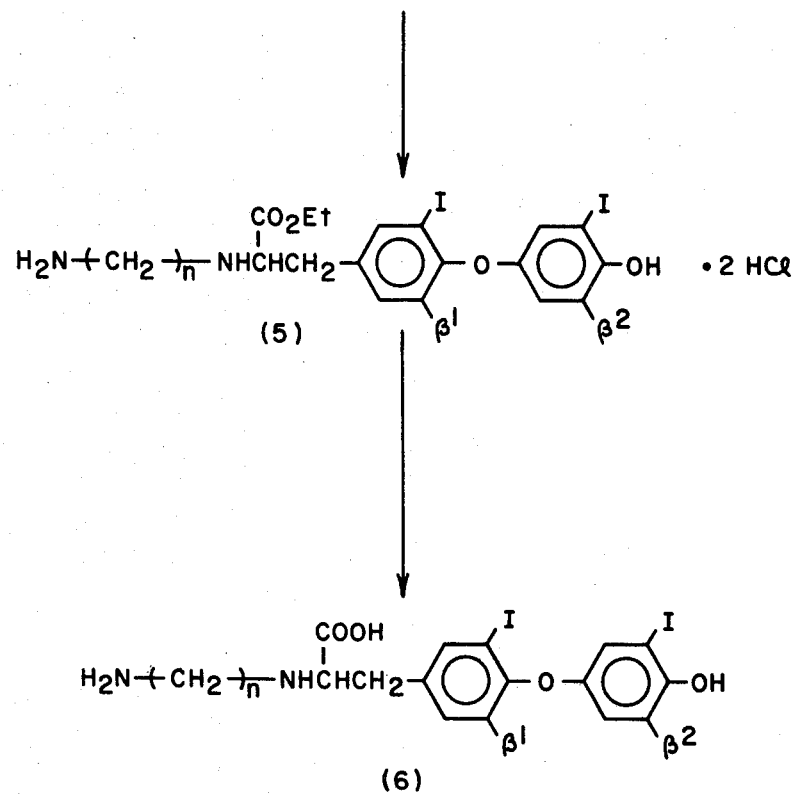

The iodothyronine derivatives are generally prepared by the route illustrated in the diagram of FIGS. 1 and 1a of the drawings. An ω-aminoalkylaldehyde diethyl acetal (1) is protected as the N-trifluoroacetate (2) by treatment with ethyl trifluoroacetate and triethylamine in an appropriate solvent, e.g., ethanol. The resulting N-trifluoroacetylalkanal diacetal is hydrolyzed to the alkylaldehyde and reacted with an iodothyronine ethyl ester (3) and sodium cyanoborohydride in an appropriate solvent, e.g., ethanol, to give the N-(ω-N-trifluoroacetylaminoalkyl) iodothyronine ethyl ester (4). Alkaline hydrolysis gives the novel N-(aminoalkyl)iodothyronine derivatives (6). Alternatively, the N-trifluoroacetyl group can be selectively removed by reflux in hydrochloric acid-saturated ethanol to give the dihydrochloride of (5) which has better organic solvent solubility properties.

The length of the linear alkyl portion of the N-aminoalkyl side arm can vary from 2 through 12 carbons by appropriate selection of the ω-aminoalkyraldehyde diethyl acetal starting material. Similarly, the alkyl ester group, if present, will vary according to the selected iodothyronine alkyl ester starting material and can be linear or branched and contain between 1 and 6 carbon atoms, e.g., methyl, ethyl, n-propyl, iso-propyl, n-butyl, sec-butyl, tert-butyl, and so forth.

The N-(aminoalkyl)iodothyronine ester derivatives (5) are converted to the corresponding acid derivatives (6) by treatment with base.

The ester and acid iodothyronine derivatives can be coupled by conventional peptide condensation reactions to carboxyl group-containing immunogenic carrier materials to yield immunogen conjugates of the formula:

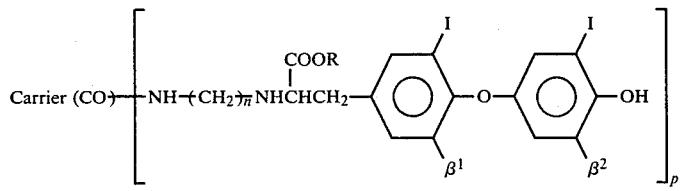

wherein Carrier (CO)— represents the carrier material bound through a carboxyl group, p is on the average from 1 through the number of available carboxyl groups on the carrier, and n, R, $\beta^1$ and $\beta^2$ are as defined above. The peptide condensation reactions available for performing the direct coupling of the iodothyronine derivative to a carboxyl group-containing carrier are well known and include, without limitation, the carbodiimide reaction [Aherne et al, *Brit. J. Clin. Pharm.* 3:56(1976) and *Science* 144:1344(1974)], the mixed anhydride reaction [Erlanger et al, *Methods in Immunology and Immunochemistry*, ed. Williams and Chase, Academic Press (New York 1967) p. 149], and the acid azide and active ester reactions [Kopple, *Peptides and Amino Acids*, W. A. Benjamin, Inc. (New York 1966)]. See also *Clin. Chem.* 22:726(1976).

Alternatively, the ester and acid iodothyronine derivatives can be coupled through the use of linking reagents that form a bond at one end with the amino group in the iodothyronine derivative and a bond at the other end with an appropriate functional group present in the carrier material. For example, bifunctional coupling reagents are well known for coupling amine derivatives to amine macromolecules, including bis-imidates, bis-isocyanates, and glutaraldehyde [*Immunochem.* 6:53(1969)]. Other useful coupling reactions are thoroughly discussed in the literature, for instance in the above-mentioned Kopple monograph; Lowe and Dean, *Affinity Chromatography*, John Wiley & Sons (New York 1974); Means and Feeney, *Chemical Modification of Proteins*, Holden-Day (San Francisco 1971); and Glazer et al, *Chemical Modification of Proteins*, Elsevier (New York 1975).

Coupling of the iodothyronine derivative to a protein or polypeptide carrier through the use of the bis-imidate bifunctional reagents is a preferred method. The resulting immunogen conjugates will comprise a linking group R' of the formula:

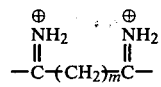

wherein m is an integer from 1 through 10 and the carrier material is coupled through an amino group. The bis-imidate coupling reagents will generally be of the formula:

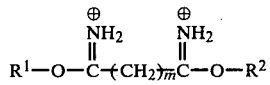

wherein m is as defined above and $R^1$ and $R^2$, which may be the same or different but which more usually are the same, are alkyl, preferably lower alkyl (i.e., having 1–4 carbon atoms) such as methyl, ethyl, n-propyl, iso-propyl, and so forth. Particularly preferred bis-imidates are the dimethyl alkylimidates, especially dimethyl adipimidate. The bis-imidates are generally available from commercial sources or may be prepared by published methods by those skilled in the art [Hunter and Ludwig, *J. Am. Chem. Soc.* 84:3491(1962)].

The bis-imidates will normally be provided in a suitable salt form which upon dissolution in the aqueous reaction media generates the positively charged bis-imidate species. Correspondingly, isolation of the immunogen conjugate from aqueous media such as by solvent evaporation or precipitation yields salts forms of the bis-imidates wherein the counter anions to the protonated imino groups are taken from available anions in the media.

The coupling reaction is allowed to proceed in aqueous solution under mild conditions, e.g., at a pH between about 7 and about 10, more usually between 8 and 9, and at temperatures between about 0° C. and about 40° C., more usually between 20° C. and 30° C. Usually, the amino-functionalized iodothyronine derivative, the bis-imidate, and the desired protein or polypeptide carrier material are added in sequence, with a short incubation period for reaction between the iodothyronine derivative and the bis-imidate of between 1 and 30 minutes, followed by addition of the protein or polypeptide and a second incubation period lasting between 10 minutes and 4 hours.

The quantity p in the above formulas represents the number of iodothyronine moieties that are conjugated to the carrier, i.e., the epitopic density of the immunogen, and in the usual situation will be on the average from 1 to about 50, more normally from 1 to about 20. Optimal epitopic densities, considering the ease and reproducibility of synthesis of the immunogen and antibody response, fall between about 2 and about 15, more usually between 4 and 10.

The immunogenic carrier material can be selected from any of those conventionally known having available functional groups for coupling to the iodothyronine amino-derivatives. In most cases, the carrier will be a protein or polypeptide, although other materials such as carbohydrates, polysaccharides, lipopolysaccharides, nucleic acids and the like of sufficient size and immunogenicity can likewise be used. For the most part, immunogenic proteins and polypeptides will have molecular weights between 4,000 and 10,000,000, preferably greater than 15,000, and more usually greater than 50,000. Generally, proteins taken from one animal species will be immunogenic when introduced into the blood stream of another species. Particularly useful proteins are albumins, globulins, enzymes, hemocyanins, glutelins, proteins having significant nonproteinaceous constituents, e.g., glycoproteins, and the like. The albumins and globulins of molecular weight between 30,000 and 200,000 are particularly preferred. Further reference for the state-of-the-art concerning conventional immunogenic carrier materials and techniques for coupling haptens thereto may be had to the following: Parker, *Radioimmunoassay of Biologically Active Compounds*, Prentice-Hall (Englewood Cliffs, New Jersey U.S.A., 1976); Butler, *J. Immunol. Meth.* 7:1–24(1974); Weinryb and Shroff, *Drug Metab. Rev.* 10:271–283(1975); Broughton and Strong, *Clin. Chem.* 22:726–732(1976); and Playfair et al, *Br. Med. Bull.* 30:24–31(1974).

Preparation of specific antibodies using the present immunogen conjugates may follow any conventional technique. Numerous texts are available describing the fundamental aspects of inducing antibody formation; for example reference may be made to Parker, *Radioimmunoassay of Biologically Active Compounds*, Prentice-Hall (Englewood Cliffs, New Jersey U.S.A., 1976). In the usual case, a host animal such as a rabbit, goat, mouse, guinea pig, or horse is injected at one or more of a variety of sites with the immunogen conjugate, normally in mixture with an adjuvant. Further injections are made at the same site or different sites at regular or irregular intervals thereafter with bleedings being taken to assess antibody titer until it is determined that optimal titer has been reached. The host animal is bled to yield a suitable volume of specific antiserum. Where desirable, purification steps may be taken to remove undesired material such as nonspecific antibodies before the antiserum is considered suitable for use in performing actual assays.

The antibodies can also be obtained by somatic cell hybridization techniques, such antibodies being commonly referred to as monoclonal antibodies. Reviews of such monoclonal antibody techniques are found in *Lymphocyte Hybridomas*, ed. Melchers et al, Springer-Verlag (New York 1978), *Nature* 266:495 (1977), and *Science* 208:692 (1980).

The present invention will now be illustrated, but is not intended to be limited, by the following examples.

EXAMPLE 1

Preparation of N-aminoalkyl iodothyronine derivatives and their alkyl esters

The reaction sequence for the preparation of these iodothyronine derivatives is shown in the diagram in FIGS. 1 and 1a of the drawings.

4-N-(Trifluoroacetyl)aminobutyraldehyde Diethylacetal (2), n=4

To a mixture of 17.74 grams (g) of 90% 4-aminobutyraldehyde diethylacetal (1) [0.1 moles (mol)] and 22.1 milliliters (ml) triethylamine (0.16 mol) in 100 ml dry ethanol at 0° C. under argon gas was added dropwise 21.3 g ethyl trifluoroacetate (0.16 mol) over 15 minutes. The mixture was allowed to warm to room temperature overnight. The reaction volume was concentrated in vacuo (bath temperature <40° C.), dissolved in ether, and washed with water and brine. Drying ($Na_2SO_4$), filtration, and evaporation of solvent in vacuo gave 25.3 g of brown oil. Fractional distillation at 104°–105° C. (0.01 mm) provided the product (2), n=4, as a colorless oil (96%, 24.6 g).

Analysis: Calculated for $C_{10}H_{18}NF_3O_3$(MW 257.26): C, 46.7; H, 6.8; N, 5.5. Found: C, 46.3; H, 7.0; N, 5.3.

PMR (60 mHz, $CDCl_3$): $\delta$1.2 (t, J=7 Hz,6H); 4.3 (m,4H); 3.2–4.0 (m,6H); 4.52 (t,J=5 Hz,1H); 7.3 (bs,1H).

IR(neat): 1705 $cm^{-1}$.

N-[4-N-(Trifluoroacetyl)aminobutyl]thyroxine Ethyl Ester (4), n=4, $\beta^1=\beta^2=I$ 4-N-(Trifluoroacetyl)aminobutyraldehyde diethylacetal (2), n=4, [3.097 g, 12 millimoles (mmol)] was stirred in a 36 ml mixture of tetrahydrofuran/acetic acid/water (1:1:1) for 48 hours under argon gas. The mixture was evaporated in vacuo to an oil which was added to 10.09 g (12 mmol) thyroxine ethyl ester hydrochloride (3), $\beta^1=\beta^2=I$, in 275 ml absolute ethanol under argon gas. Sodium cyanoborohydride [422 milligrams (mg), 6.8 mmol] was added to the mixture, which was allowed to stir 24 hours at room temperature. The mixture was filtered and concentrated in vacuo to a foam, which was dissolved in 40 ml 20% ethyl acetate-dichloromethane, filtered, and allowed to stand overnight. White crystals of product appeared which were collected, washed with dichloromethane, and dried to yield 4.32 g (37%), mp 202°–204° C.

Analysis: Calculated for $C_{23}H_{22}N_2F_3I_4O_5.2H_2O$ (MW 1008.12): C, 27.40; H, 2.70; N, 2.78. Found: C, 27.36; H, 2.45; N, 2.77.

PMR (60 mHZ, DMSO-$d_6$): $\delta$1.13(t,J=3 Hz, 3H); 1.67 (m,4H); 2.7–3.9 (m,6H); 4.2 (m+superimposed q, J=7 Hz,3H); 7.12 (s,2H), 7.92 (s,2H); 9.65 (m,3H).

IR (KCl): 1720, 1745 $cm^{-1}$.

The mother liquor was concentrated in vacuo, dissolved in 10 ml ethyl acetate, and chromatographed on a Waters Prep 500 ® HPLC (Waters Associates, Inc., Milford, MA) using one Prep-Pak-500 ® 5.7 ID×30 cm silica cartridge (Waters Associates, Inc., Milford, MA) as a stationary phase and 20% ethyl acetatedichloromethane as the mobile phase.

First eluted from the column was an oil which was precipitated as a white powder (1.1 g) from dichloromethane-hexane, mp 64°–68° C. decomposed. It was identified as N,N-bis-[4-N-(trifluoroacetyl)aminobutyl]-thyroxine ethyl ester on the basis of the following analytical data (7% yield).

Analysis: Calculated for $C_{29}H_{31}N_3F_6I_4O_6.H_2O$ (MW 1157.24): C, 30.10; H, 2.87; N, 3.63. Found: C, 30.01; H, 2.45; N, 4.13.

PMR (60 mHZ, DMSO-$d_6$): $\delta$1.15 (m+bt, J=7 Hz,7H); 1.65 (m,4H); 2.9 (m,3H); 3.2 (m,4H); 3.7 (m,3H); 4.1 (m+q, J=7 Hz, 3H); 5.73 (m,2H); 7.13 (s,2H); 7.88 (s,2H); 9.4 (m,1H).

IR (KCl): 1720 $cm^{-1}$.

Next obtained from the column was an oil, which was precipitated as 3.886 g of a white powder from dichloromethane-hexane. Spectral data showed it to be identical with the initially formed crystals. The total yield of product (4), n=4, $\beta^1=\beta^2=I$, was 8.23 g (71%), mp 105°–106°.

Analysis: Calculated for $C_{23}H_{23}N_2O_5I_4F_3$ (MW 972.09): C, 28.41; H, 2.39; N, 2.88. Found: C, 28.33; H, 2.40; N, 2.78.

N-(4-Aminobutyl)thyroxine Ethyl Ester Bishydrochloride (5), n=4, $\beta^1=\beta^2=I$.

N-[4-N-(Trifluoroacetyl)aminobutyl]thyroxine ethyl ester (4), n=4, $\beta^1=\beta^2=I$, (2.5 g, 2.6 mmol) was dissolved in 100 ml anhydrous ethanol. The solution was heated to reflux while treated with gaseous hydrochloric acid for 7 hours. The mixture was concentrated in vacuo and the residue twice precipitated from ethanol-ether to give 2.115 g of an off-white powder (79% yield) which analyzed as the bishydrochloride diethanolate (5), n=4, $\beta^1=\beta^2=I$.

Analysis: Calculated for $C_{21}H_{24}N_2I_4O_4.2HCl.2(C_2H_6O)$ (MW 1041.13): C, 28.84; H, 3.68; N, 2.69. Found: C, 29.32; H, 3.28; N, 2.91.

PMR (90 mHZ, DMSO-$d_6$): $\delta$1.13 (t, J=7 Hz); 1.77 (m); 3.29 (m); 3.66 (m); 4.67 (m); 7.17 (s); 7.88 (s); 8.79 (m); 10.0 (m); 10.6 (m).

IR (KCl): 1735, 2970 cm$^{-1}$.

N-(4-Aminobutyl)thyroxine (6), n=4, $\beta^1=\beta^2=I$

N-[4-N-(Trifluoroacetyl)aminobutyl]thyroxine ethyl ester (4), n=4, $\beta^1=\beta^2=I$, 2.0 g (2.06 mmol) was dissolved in 20 ml tetrahydrofuran under argon gas and treated with 4.1 ml of a 2 N sodium hydroxide solution. The mixture was stirred overnight at 50° C. The reaction mixture was then preadsorbed onto a small amount of Silicar CC-7 (silicic acid; Mallinkrodt, Inc., Paris, KY) and applied to the top of a column of 175 g Silicar CC-7 packed with the lower phase of a 2:1:1 chloroform-methanol-ammonium hydroxide mixture. The column was sequentially eluted with 3 liters each of the lower phase of a 2:1:1 and 1:1:1 chloroform-methanol-ammonium hydroxide mixture. The off-white powder obtained was dissolved in ethanol and 5 ml 2 N sodium hydroxide, treated with Norit filtered through celite, and was precipitated with acetic acid. Obtained was 1.5 g (88% yield) of the conjugate (6), $\beta^1=\beta^2=I$, as amorphous powder, mp 166° decomposed.

Analysis: Calculated for $C_{19}H_{20}I_4O_3.H_2O$ (MW 850.05): C, 26.85; H, 2.61; N, 3.30. Found: C, 26.47; H, 2.51; N, 3.29.

PMR (100 mHz, $CD_3OD+Na°$): $\delta$1.48 (m); 2.64 (m); 2.82 (dd,J=6 Hz, 8 Hz); 3.26 (t,J=6 Hz); 7.04 (s); 7.86 (s).

IR (KCl): 1640, 1435, and 1505 cm$^{-1}$.

The hydrochloride was prepared by stirring 100 mg of the product in 6 ml of 6 N hydrochloric acid for 2 hours at reflux under argon gas. Filtration and drying at 55° C. (0.1 mm Hg) for 17 hours gave 82 mg of the product (79% yield).

Analysis: Calculated for $C_{19}H_{20}N_2I_4O_3.HCl.H_2O$ (MW 886.50): C, 25.74; H, 2.62; N, 3.16. Found: C, 25.87; H, 2.34; N, 3.17.

EXAMPLE 2

Preparation of antibodies to thyroxine using bis-imidate coupled immunogen

Eighty-three milligrams of N-(4-aminobutyl)thyroxine (Example 1) was added to 3.0 ml of 0.1 M sodium carbonate, and 35 μl of 0.1 N sodium hydroxide was added. Dimethyladipimidate dihydrochloride (90 mg) was added and a precipitate formed. The precipitate dissolved upon addition of 70 μl of 10 N sodium hydroxide. When this reaction mixture had stood at room temperature for 3 to 5 minutes, it was added dropwise to a stirred solution containing 200 mg of bovine serum albumin in 50 ml of 0.2 N sodium hydroxide. This mixture was allowed to stand at room temperature for 2.5 hours and then the pH was adjusted to 7.0 with 5 N hydrochloric acid. The precipitate which formed was removed by centrifugation, and the supernatant was concentrated to 5-7 ml by pressure dialysis.

The concentrate was chromatographed on a 2.5×45 cm column of Sephadex G25 (coarse) equilibrated with 0.1 M sodium phosphate, pH 7.0 containing 0.02% sodium azide. About 12 ml fractions were collected and fractions 9–12 were pooled.

Two-tenths milliliter of the pool was diluted into 0.8 ml of 0.1 N sodium hydroxide, and the optical absorption spectrum from 260 to 360 nanometers (nm) was recorded. An absorption maximum occurred at 328 nm. The absorbances at 280 and 328 nm were used to estimate an incorporation of 6.8 moles of N-(4-aminobutyl)-thyroxine per mole of bovine serum albumin.

The N-(4-aminobutyl)thyroxine bovine serum albumin conjugate pool was diluted to give 0.6 mg conjugate per ml. For the initial immunization, this solution was blended with an equal volume of Freund's complete adjuvant. One-tenth milliliter of the mixture was injected subcutaneously into each foot pad of a rabbit and 0.6 ml was injected subcutaneously on the back of the rabbit. Booster immunizations were administered on the back 3, 7, 11, and 15 weeks later. These immunizations employed Freunds incomplete adjuvant. Blood was drawn on the 16th week and serum was collected by centrifugation.

Antibody binding reaction mixtures were prepared for titrating the thyroxine antibodies by combining reagents in the order presented in Table A. The $^{125}I$ labeled thyroxine (Tetramat, Abbott Laboratories, Inc., Chicago, IL) gave about 630,000 counts per minute (cpm) per ml when measured on a Gammacord ® crystal scintillation instrument (Ames Division, Miles Laboratories, Inc., Elkhart, IN). All of the reagents were prepared in 0.1 M sodium phosphate buffer, pH 7.0. The antibody was allowed to incubate with the $^{125}I$-thyroxine for 2 to 3 hours at room temperature before the 50% polyethylene glycol was added. After the polyethyleneglycol was added and mixed, insoluble proteins were sedimented by centrifugation and the supernatant was decanted. The radioactivity in the pellet was measured.

TABLE A

| 0.1M Sodium Phosphate pH 7.0 (μl) | Normal Rabbit Immuno-globulin (μl) | Antiserum to Thyroxine (5 μl/ml) (μl) | $^{125}I$-Thyroxine (μl) | 50% Poly-Ethylene glycol (μl) | Radio-activity (cpm) |
|---|---|---|---|---|---|
| 480 | 20 | — | 100 | 400 | 4600 |
| 470 | 20 | 10 | 100 | 400 | 39,100 |
| 460 | 20 | 20 | 100 | 400 | 41,600 |
| 380 | 20 | 100 | 100 | 400 | 43,500 |

EXAMPLE 3

Thyroxine Radioimmunoassay

Competitive binding reaction mixture were prepared with various levels of thyroxine by combining reagents in the order presented in Table B (the antiserum used having been raised against the bis-imidate coupled immunogen of Example 2). The $^{125}$I-thyroxine solution gave about 450,000 counts per minute (cpm) per ml. The reactions were allowed to incubate at room temperature for 2 to 3 hours before the 50% polyethyleneglycol was added. The insoluble proteins were collected as outlined above and the radioactivity was measured.

The results show that as the level of thyroxine increased, the amount $^{125}$I-thyroxine bound to antibody decreased.

TABLE B

| 0.1M Sodium Phosphate pH 7.0 (μl) | Normal Rabbit Immunoglobulin (μl) | $^{125}$I-Thyroxine (μl) | Thyroxine (5 μM) (μl) | Antiserum to Thyroxine (5 μl/ml) (μl) | 50% Poly-Ethyleneglycol (μl) | Radioactivity cpm |
|---|---|---|---|---|---|---|
| 480 | 20 | 100 | — | — | 400 | 4,700 |
| 380 | 20 | 100 | — | 100 | 400 | 22,000 |
| 380 | 20 | 100 | 1 | 100 | 400 | 13,100 |
| 380 | 20 | 100 | 2 | 100 | 400 | 10,600 |
| 380 | 20 | 100 | 3 | 100 | 400 | 6,400 |
| 330 | 20 | 100 | 50 | 100 | 400 | 3,900 |

EXAMPLE 4

Nonradioisotopic immunoassay for thyroxine

Reaction mixtures were formed by combining NADPH, buffer, thyroxine antibody (Example 2) and varying levels of thyroxine in the amounts and concentrations indicated in Table C and incubated at room temperature for a minimum of 30 seconds. Then 100 μl of 0.16 μM methotrexate-aminobutyl thyroxine conjugate [prepared from N-(4-aminobutyl)thyroxine ethyl ester bishydrochloride (5), n=4, $\beta^1=\beta^2=$I, supra, as described in U.S. Patent Application Ser. No. 318,028, filed on Nov. 4, 1981 and assigned to the present assignee] was added and the mixture was incubated at room temperature for 2 minutes. Following the second incubation, dihydrofolate reductase was added and the mixture incubated an additional 5 minutes at 37° C. The reaction was initiated by adding dihydrofolate and an initial absorbance at 340 nm was recorded. The reaction was allowed to proceed for 20 minutes at 37° C. and a final reading of absorbance recorded. The results in Table C show that the enzyme activity (ΔA) decreased as the thyroxine level increased.

EXAMPLE 5

Preparation of antibodies to thyroxine using directly coupled immunogen

An immunogen was prepared by coupling the primary amino group of N-(4-aminobutyl)thyroxine to the carboxyl groups of bovine serum albumin. The protein (151 mg dissolved in 3 ml water) was cooled in an ice bath. N-(4-aminobutyl)thyroxine ethyl ester (39 mg) was dissolved in 5 ml of water and added to the protein solution. The pH was 4.3. 1-Ethyl-3-(3-dimethylaminopropyl)-carbodiimide (202 mg dissolved in 2 ml of water) was cooled and added dropwise to the albumin, N-(4-aminobutyl)thyroxine solution. The pH was 5.1 and was adjusted to 4.6 with 0.1 M HCl.

The reaction was allowed to proceed for 5 hours at 4° C. Then the reaction mixture was applied to a 3×50 cm column of Sephadex G-50 (fine) equilibrated with 50 mM sodium acetate buffer, pH 5.0. Four milliliter fractions were collected and the first eluted peak of material with absorbance at 280 nm was pooled and dialyzed against 0.15 M sodium chloride.

This immunogen had 6.0 moles of thyroxine residues per mole of bovine serum albumin.

The ester function of the thyroxine residues was hydrolyzed with alkali. Twenty-five milliliters of the dialyzed immunogen was combined with 0.25 ml 1 M sodium hydroxide which gave a pH of 12. This mixture was allowed to stand at room temperature for 18 hours. Then the solution was adjusted to pH 7.5 with 1 M HCl.

Four milliliters of immunogen (1 mg/ml) was combined with 10 ml of Freunds complete adjuvant and 2 ml of saline. Rabbits were immunized subcutaneously each with 2 ml of this mixture. Three weeks later they were reimmunized with the same mixture prepared with incomplete Freunds adjuvant. The booster immunizations were repeated every 4 weeks. Test bleedings were taken one week after the boosters. Antiserum with suitable titers were obtained by 4 months after the initial immunization.

TABLE C

| 0.1M Sodium Phosphate Buffer pH 6.0 (μl) | Thyroxine 1 × 10$^{-7}$M (μl) | Antibody to Thyroxine 1:4 Dil (μl) | Methotrexate-Aminobutyl-Thyroxine 0.16 μM (μl) | NADPH 2.1 mM (μl) | Dihydrofolate Reductase 0.04 U/ml (μl) | Dihydrofolate 0.5 mM (μl) | ΔA$_{340}$/ 20 Min |
|---|---|---|---|---|---|---|---|
| 1800 | — | — | — | 95 | 50 | 55 | 0.620 |
| 1700 | — | — | 100 | 95 | 50 | 55 | 0.458 |
| 1670 | — | 30 | 100 | 95 | 50 | 55 | 0.645 |
| 1650 | 20 | 30 | 100 | 95 | 50 | 55 | 0.637 |
| 1630 | 40 | 30 | 100 | 95 | 50 | 55 | 0.610 |
| 1590 | 80 | 30 | 100 | 95 | 50 | 55 | 0.595 |
| 1550 | 120 | 30 | 100 | 95 | 50 | 55 | 0.595 |
| 1510 | 160 | 30 | 100 | 95 | 50 | 55 | 0.585 |
| 1470 | 200 | 30 | 100 | 95 | 50 | 55 | 0.584 |

EXAMPLE 6

Titration of thyroxine antibodies

The following reagents were prepared.

Buffer—0.1 M sodium phosphate, pH 7.0, containing 0.1% (w/v) bovine serum albumin and 0.1% (w/v) sodium azide.

Thyroxine—200 ng thyroxine/ml of the 0.1 M sodium phosphate buffer, pH 7.0.

Antiserum to Thyroxine—The antiserum (from Example 5) was diluted into 0.1 M sodium phosphate buffer, pH 7.0, such that 20 ml aliquots added to the assay gave antiserum levels indicated in the table below.

Composite Reagent—0.1 M sodium phosphate buffer, pH 7.0, containing 0.1% (w/v) sodium azide, 0.125 M glucose, 2.5 mM 2-hydroxy-3,5-dichlorobenzene sulfonate, 1.25% (w/v) bovine serum albumin and 23.8 μg horseradish peroxidase/ml.

Apoglucose Oxidase Reagent—0.1 M sodium phosphate buffer, pH 7.0, 6.0 μM apoglucose oxidase binding sites (see U.S. Pat. No. 4,268,631), 12 mM 4-amino antipyrine, 0.1% (w/v) sodium azide, 400 μl antiserum to glucose oxidase/ml 30% (v/v) glycerol.

FAD-Thyroxine—0.1 M sodium phosphate buffer, pH 7.0, containing 40 nM flavin adenine dinucleotide conjugate. The conjugate was prepared as described in U.S. Pat. No. 4,171,432.

Two series of cuvettes (12 each) were designated A and B. Buffer (0.23 ml) was added to sets A and B. Fifty microliter of the Thyroxine Reagent was added to each cuvette in set B.

Antiserum was added to cuvettes in each set such that the levels given in the table below were achieved. The cuvettes were allowed to stand at ambient temperature for at least 5 minutes.

One and six-tenths mililiters of Composite Reagent was added to each cuvette. Then 50 μl of FAD-thyroxine was added followed immediately by 50 μl of Apoglucose Oxidase Reagent. The reactions were incubated at 37° C. for 15 minutes and then the absorbance at 520 nM was recorded.

The results were as follows:

| Antiserum | Absorbances at 520 nM | |
|---|---|---|
| (μl/assay) | set A | set B |
| 0 | 1.06 | 1.10 |
| 2.5 | 0.614 | 0.778 |
| 5.0 | 0.394 | 0.530 |
| 7.5 | 0.375 | 0.445 |
| 10.0 | 0.326 | 0.335 |
| 20.0 | 0.107 | 0.110 |

The results from set A show that the glucose oxidase activity decreased as the antibody level increased indicating that the antibody inactivated the flavin adenine dinucleotide thyroxine conjugate. In the presence of thyroxine, set B, the absorbances were higher indicating that thyroxine and the conjugate competed for antibody binding sites.

What is claimed is:

1. An iodothyronine immunogen conjugate of the formula:

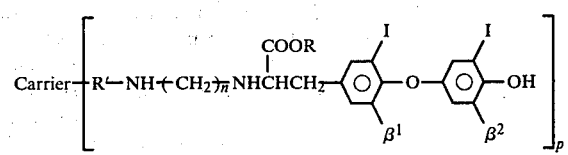

wherein Carrier is an immunogenic carrier material, R' is a bond or a linking group, n is an integer from 2 through 12, p is on the average from 1 through about 50, R is hydrogen or alkyl containing 1-6 carbon atoms, and $\beta^1$ and $\beta^2$ are, independently, hydrogen or iodine.

2. The conjugate of claim 1 wherein R' is a bond or a chain comprising between 1 and 20 atoms excluding hydrogen.

3. The conjugate of claim 1 wherein R' is a bond and the carrier material is coupled through carboxyl groups of the carrier material.

4. The conjugate of claim 1 wherein R' is a linking group of the formula:

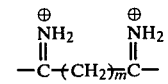

wherein m is an integer from 1 through 10 and the carrier material is coupled through amino groups.

5. The conjugate of claim 1 wherein R is hydrogen.

6. The conjugate of claim 1 wherein R is ethyl.

7. The conjugate of claim 5 or 6 wherein n=4.

8. The conjugate of any one of claims 1-4 wherein $\beta^1$ and $\beta^2$ are both iodine.

9. An iodothyronine immunogen conjugate of the formula:

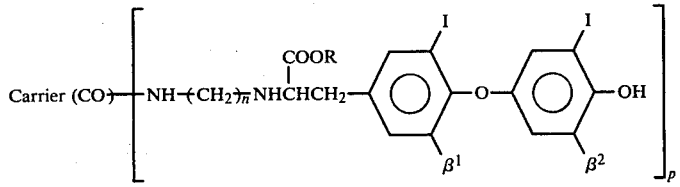

wherein Carrier (CO)—represents an immunogenic protein or polypeptide carrier material bound through a carboxyl group, n is an integer from 2 through 12, p is on the average from 1 through the number of available carboxyl groups on said carrier material, R is hydrogen or alkyl containing 1-6 carbon atoms, and $\beta^1$ and $\beta^2$ are, indpendently, hydrogen or iodine.

10. The conjugate of claim 9 wherein R is hydrogen.

11. The conjugate of claim 9 wherein R is alkyl containing 1-6 carbon atoms.

12. The conjugate of claim 11 wherein R is ethyl.

13. The conjugate of any one of claims 9-12 wherein n is 4.

14. The conjugate of any one of claims 9-12 wherein $\beta^1$ and $\beta^2$ are both iodine.

15. The conjugate of claim 9 wherein p is on the average from 1 through 20.

16. The conjugate of claim 9 wherein said carrier material is an albumin.

17. An antibody prepared against the conjugate of claim 1.

18. An antibody prepared against the conjugate of claim 3.

19. An antibody prepared against the conjugate of claim 4.

20. An antibody prepared against the conjugate of claim 8.

21. An antibody prepared against the conjugate of claim 9.

22. An antibody prepared against the conjugate of claim 13.

23. An antibody prepared against the conjugate of claim 14.

* * * * *